(12) United States Patent
Smith et al.

(10) Patent No.: US 7,895,863 B2
(45) Date of Patent: Mar. 1, 2011

(54) GRADIENT COMPRESSION HOSIERY KNITTED USING CORESPUN YARNS

(75) Inventors: Mark W. L. Smith, DeSoto, KS (US); Jeffrey C. Dalbey, Leawood, KS (US)

(73) Assignee: Knit-Rite, Inc., Kansas City, KS (US)

( * ) Notice: Subject to any disclaimer, the term of this patent is extended or adjusted under 35 U.S.C. 154(b) by 0 days.

(21) Appl. No.: 12/499,358

(22) Filed: Jul. 8, 2009

(65) Prior Publication Data

US 2010/0005568 A1    Jan. 14, 2010

Related U.S. Application Data

(60) Provisional application No. 61/079,039, filed on Jul. 8, 2008.

(51) Int. Cl.
*A41B 11/00* (2006.01)
(52) U.S. Cl. .......................................... 66/172 E; 66/183
(58) Field of Classification Search .................. 66/172 E, 66/178 A, 183
See application file for complete search history.

(56) References Cited

U.S. PATENT DOCUMENTS

| | | | | |
|---|---|---|---|---|
| 3,889,494 A | * | 6/1975 | Patience et al. | 66/178 R |
| 4,027,667 A | | 6/1977 | Swallow et al. | |
| 4,172,456 A | * | 10/1979 | Zens | 602/63 |
| 4,180,065 A | * | 12/1979 | Bowen | 66/172 E |
| 4,502,301 A | * | 3/1985 | Swallow et al. | 66/178 A |
| 6,158,253 A | | 12/2000 | Svoboda et al. | |
| 6,430,970 B1 | * | 8/2002 | Gardon-Mollard et al. | 66/178 A |
| 7,363,778 B2 | | 4/2008 | Pickering et al. | |
| 7,575,561 B2 | | 8/2009 | Smith et al. | |
| 2002/0108405 A1 | | 8/2002 | Yakopson | |
| 2007/0283483 A1 | | 12/2007 | Jacober | |

FOREIGN PATENT DOCUMENTS

GB          448071          6/1936

OTHER PUBLICATIONS

International Search Report and Written Opinion from corresponding PCT Application No. PCT/US2009/049939 (dated Sep. 8, 2009).
"Knitted Stretch Technology", edited by Charles Reichman, published by National Knitted Outerwear Association, front cover, all pages preceding p. 1, pp. 3-11 and 73-108 (1965).

* cited by examiner

*Primary Examiner* — Danny Worrell
(74) *Attorney, Agent, or Firm* — Hovey Williams LLP

(57) ABSTRACT

Gradient compression hosiery with therapeutic and aesthetic properties broadly includes a stocking section extending continuously between a distal end and an open proximal end thereof. The stocking section includes a tubular foot portion and a tubular leg portion. The stocking section is knitted at least substantially of a core-spun yarn with an elastomeric core and a twisted fiber sheath and includes elastomeric threads integrated into the stretch yarn knitting. The stocking section further presents a gradient region that extends from a distal location adjacent the distal end to a proximal location adjacent the proximal end, with a property of the hosiery changing progressively along the gradient region to provide compression that decreases progressively from the distal location to the proximal location when the hosiery is donned.

22 Claims, 2 Drawing Sheets

GRADIENT COMPRESSION HOSIERY KNITTED USING CORESPUN YARNS

RELATED APPLICATION

This application claims the benefit of U.S. Provisional Application Ser. No. 61/079,039, filed Jul. 8, 2008, entitled GRADIENT COMPRESSION HOSIERY KNITTED USING CORESPUN YARNS, which is hereby incorporated in its entirety by reference herein.

BACKGROUND

1. Field

The present invention relates generally to knitted garments. More specifically, embodiments of the present invention concern knitted gradient compression hosiery that is comfortable and easy to don while providing therapeutic and aesthetic benefits.

2. Discussion of Prior Art

Gradient compression hosiery is used to provide variable compressive pressure that decreases gradually from the ankle in a proximal direction along a wearer's leg. Such hosiery is known to minimize blood pooling in the leg and other symptoms associated with certain venous and lymphatic disorders, fatigue, and adverse environmental conditions.

While prior art gradient compression hosiery provides therapeutic relief of the above-noted symptoms, such hosiery has particular unresolved deficiencies. It has been found that conventional, tight-fitting, gradient compression hosiery requires significant strength for the wearer to expand and pull the hosiery onto the leg, thus making the hosiery difficult for the wearer to don. Moreover, prior art gradient compression hosiery has been found to ineffectively conform to the wearer's leg when donned.

SUMMARY

Embodiments of the present invention provide gradient compression hosiery that does not suffer from the problems and limitations of the prior art hosiery set forth above.

One aspect of the present invention concerns gradient compression hosiery operable to be received on the lower limb of a wearer and provide compression to the lower limb that varies along the length of the limb. The gradient compression hosiery broadly includes a stocking section that extends continuously between a distal end and an open proximal end thereof. The stocking section includes a tubular foot portion extending from the distal end and a tubular leg portion extending from the open proximal end, with the foot portion dimensioned to receive the foot of the wearer and the leg portion dimensioned to receive at least part of the leg of the wearer when the hosiery is donned. The stocking section is knitted at least substantially of a stretch yarn and includes elastomeric threads integrated into the stretch yarn knitting, with the foot portion and leg portion being configured to be undersized relative to the foot and leg of the wearer. The stocking section presents a gradient region that extends from a distal location adjacent the distal end to a proximal location adjacent the proximal end, with a property of the hosiery changing progressively along the gradient region to provide compression that decreases progressively from the distal location to the proximal location when the hosiery is donned. The stretch yarn comprises a core-spun yarn that includes an elastomeric core and a twisted fiber sheath.

Other aspects and advantages of the present invention will be apparent from the following detailed description of the preferred embodiments and the accompanying drawing figures.

BRIEF DESCRIPTION OF THE DRAWING FIGURES

Preferred embodiments of the invention are described in detail below with reference to the attached drawing figures, wherein.

Figure 1:
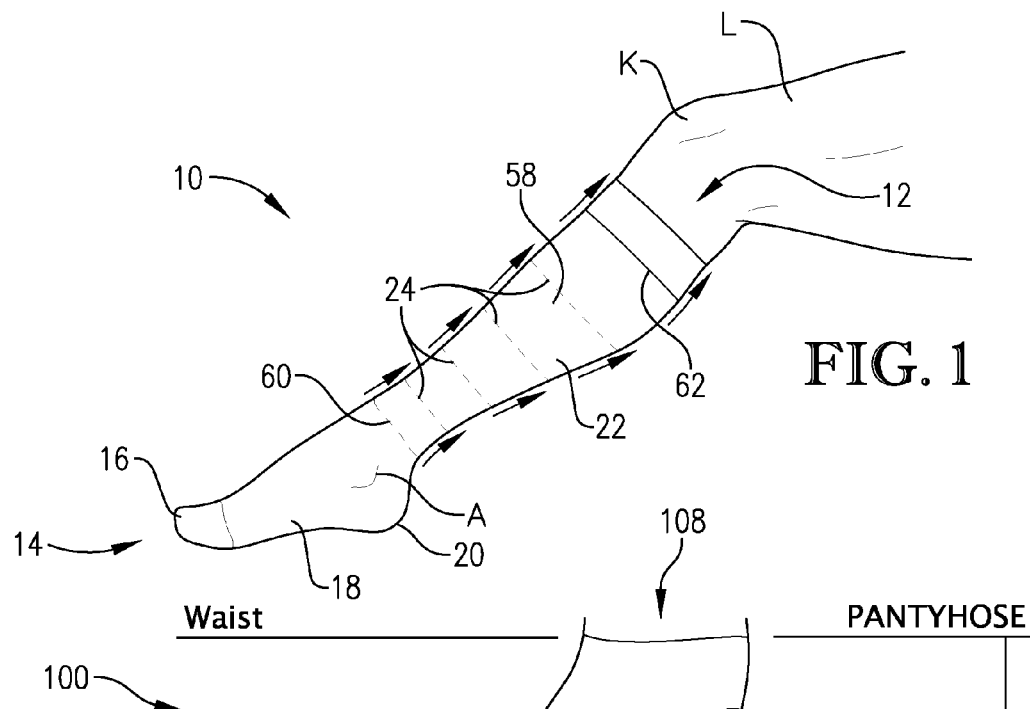
FIG. 1 is a left side view of a knitted gradient compression knee length sock constructed in accordance with a first preferred embodiment of the present invention and showing compression that decreases in a proximal direction from the ankle of the wearer's lower limb.

The drawing figures do not limit the present invention to the specific embodiments disclosed and described herein. The drawings are not necessarily to scale, emphasis instead being placed upon clearly illustrating the principles of the preferred embodiment.

DETAILED DESCRIPTION OF THE PREFERRED EMBODIMENTS

Turning initially to FIG. 1, a knitted gradient compression hosiery 10 in the form of a trouser sock includes a proximal open end 12 and a distal closed toe end 14, and is received on a wearer's lower limb L below the knee K to provide therapeutic support for various conditions while being comfortable to don and wear. As will be shown in the alternative embodiment depicted in FIG. 2, the sock 10 can also be configured with different lengths such that the proximal end of the hosiery can be spaced at different points upwardly from the knee and can also be configured as pantyhose.

Figure 3:
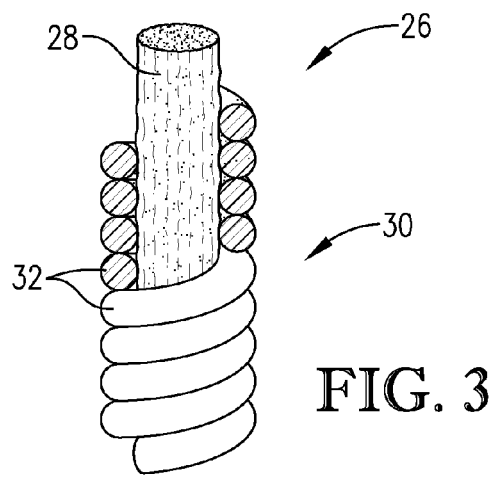
FIG. 3 is a greatly enlarged view of a core-spun stretch yarn depicted in an elongated condition and including an elastomeric core and a partly cross-sectioned twisted fiber sheath wrapped around the core.

Turning to FIGS. 1 and 3, the sock 10 includes a toe section 16 adjacent the toe end 14, a foot section 18, a heel section 20, and a lower leg section 22, as will be discussed in greater detail. The sock 10 comprises a weft-knitted receptacle that is knitted into multiple courses 24 (several of which are shown schematically), with the courses 24 preferably including a core-spun yarn 26. The illustrated sock 10 also preferably includes a laid-in elastomeric thread (not shown) that is laid into courses 24. Preferably, the elastomeric thread comprises a double-covered Lycra® spandex, as will be discussed further, and is integrated into the courses 24 with a pre-tension applied. However, it is within the scope of the present invention where other elastomeric threads, such as a single-covered spandex, are used in the sock 10. Furthermore, the elastomeric thread could be alternatively integrated into courses 24, e.g., by being knit into the courses 24 simultaneously with the core-spun yarn 26. As will be discussed, the elastomeric thread is integrated with a pre-tension that gradually decreases in a proximal direction.

Turning to FIG. 3, the core-spun yarn 26 is shown in an elongated condition and includes a spandex core 28 and a non-elastomeric sheath 30. The illustrated sheath 30 comprises a twisted thread 32 with a Z-twist but, as will be discussed in greater detail, the preferred sock 10 includes multiple core-spun yarns with alternating yarns of S-twist and Z-twist thread sheath. The core 28 preferably includes a spandex material because of its elastomeric properties. More preferably, the core 28 comprises Lycra® spandex material. For some aspects of the present invention, the core 28 could include another elastomeric fiber without departing from the scope of the present invention.

The twisted thread 32 of sheath 30 is wrapped around the core 28 with a Z-twist. However, the sock 10 is knitted with an equal number of ends of Z-twist and S-twist core-spun yarns 26. In this way, the opposite torsional bias of the Z-twist and S-twist yarns cancel each other out to restrict twisting of the sock 10. Preferably, the thread 32 comprises a non-elastomeric moisture wicking polyester or polyester blend. Most preferably, the thread 32 comprises a CoolMax® polyester material. However, it is also within the scope of the present invention where thread 32 includes another twisted fiber sheath, such as a wool blended yarn, a spun nylon yarn, or another polyester yarn (such as an X-STATIC® polyester blended yarn as will be discussed below). For example, features of an alternative core-spun yarn knitted into a weft-knitted article are disclosed in U.S. Pat. No. 6,158,253, issued Dec. 12, 2000, entitled SEAMLESS, FORM FITTING FOOT SOCK, which is hereby incorporated in its entirety by reference herein.

Figure 4:
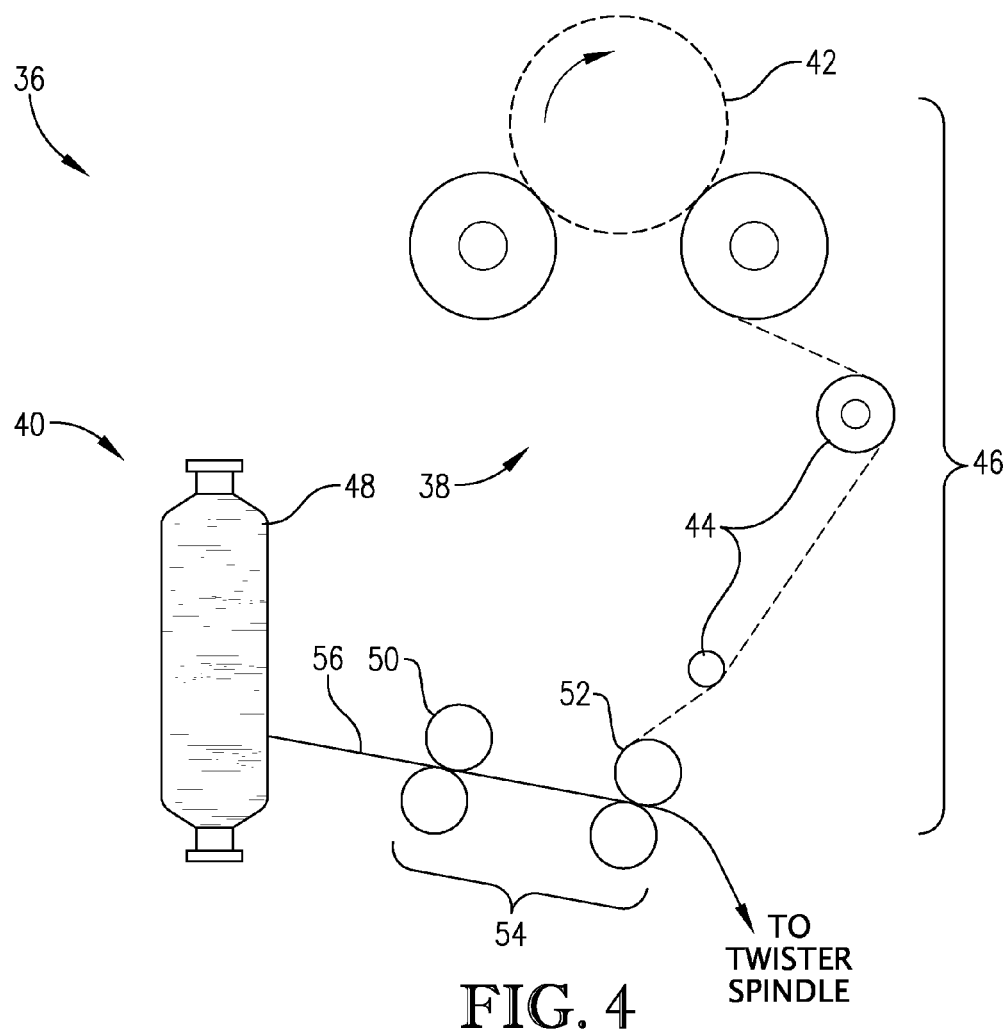
FIG. 4 is a schematic view of a machine for spinning the twisted fiber sheath around the elastomeric core.

Turning to FIG. 4, core-spun yarn 26 is preferably manufactured using a core-spinning machine 36. The machine includes a core portion 38 and a sheath portion 40. The core portion 38 includes a spandex roll 42 and guide rolls 44 that provide a spandex draft zone 46 for feeding the spandex core 28 and producing a draft (i.e., pre-tension) in the spandex core 28. The sheath portion 40 includes a fiber sheath spool 48 in roving form and guide rollers 50,52 that provide a sheath draft zone 54 for feeding sheath thread 56 and producing a draft in the sheath thread 56. The spandex core 28 and sheath thread 56 are both fed through guide rollers 50 and fed to a twister spindle (not shown). It is also within the ambit of the present invention to use an alternative spinning machine to produce the core-spun yarn 26. As will be discussed, the sock 10 is preferably knitted with core-spun yarn 26 and laid-in elastomeric thread (not shown), but could be knit on another machine (such as a flat bed knitting machine) without departing from the scope of the present invention.

Turning again to FIG. 1, the sock 10 presents a gradient compression region 58 that extends proximally from a distal location 60 above the heel portion (and adjacent the user's ankle A) along the lower leg section 22 to a proximal location 62 adjacent the proximal open end 12. Preferably, the gradient compression region 58 provides compression to the limb L that decreases progressively from the distal location 60 to the proximal location 62.

Preferably, the sock 10 has a measured stocking compression that is measured in a designated circumference range of the sock, with the measured stocking compression decreasing progressively from the distal location 60 to the proximal location 62. Such measurements are typically performed by compression measurement equipment manufactured by Instron or Bolam Corporation. Preferably, the stocking compression ranges from about 10 mmHg to about 40 mmHg. More preferably, stocking compression is divided into categories: light (10-15 mmHg), mild (15-20 mmHg), moderate (20-30 mmHg), and firm compression (30-40 mmHg) to treat circulatory and vascular medical conditions as well as tired, sore, swollen, or aching legs. While not common, the principles of the present invention are applicable where sock 10 exhibits compression above 40 mmHg. Light compression hosiery is generally preferred for tired, aching, or fatigued legs (e.g., due to long periods of standing or sitting). Moderate compression hosiery is generally preferred for patients with chronic conditions like varicose veins or phlebitis. Finn compression hosiery is generally prescribed for conditions such as clotting, mild to serious lymphedema, post-phlebitis syndrome, severe venous insufficiency, venous statis, deep vein thrombosis, or pulmonary embolisms.

Compression is preferably provided in the gradient compression region 58 by a combination of properties, some of which generally do not vary along the length of the sock 10. For example, as will be shown in greater detail below, compression can be adjusted to provide a desired compression range (as discussed above and shown in Table 2 below) by selecting the thread denier of the elastomeric laid-in thread. It is also within the scope of the present invention to provide the desired compression range by selecting an alternative denier of the spandex core 28.

Furthermore, gradient compression in the region 58 can be selectively varied along the length of the sock 10 by changing a property of the sock 10 progressively along the region 58 (e.g., to provide compression that decreases progressively from the distal location 60 to the proximal location 62). In particular, gradient compression is preferably provided by a combination of properties that can be varied along the sock 10. For example, gradient compression is preferably provided by progressively increasing the stitch size of the stretch yarn knitting (i.e., the knitted core-spun yarn) from the distal location 60 to the proximal location 62. Furthermore, gradient compression is also preferably provided by adjusting the pre-tension of the integrated elastomeric thread. In particular, the thread pre-tension is progressively decreased from the distal location 60 to the proximal location 62 as the thread is integrated into the region 58. While this combination of varying properties that change progressively along the region 58 is preferred, it is also within the ambit of the present invention where only one of the properties is varied to provide gradient compression (e.g., where stitch size is constant along the sock 10).

It has been found that the combination of core-spun yarn 26 and laid-in elastomeric thread is operable to provide greater stretch in the above-listed compression ranges when compared to conventional nylon, non-core-spun, gradient compression hosiery. Using a Jones Cross Stretch Machine and a length stretch machine, resistance and maximum stretch measurements were collected for a conventional microfiber nylon sock and a preferred configuration of a core-spun compression sock 10 (see Table 1).

In particular, the leg and foot sections of the preferred core-spun sock 10 include core-spun yarns with a Lycra® spandex core 28 and a CoolMax® polyester sheath 30. As discussed previously, the sheath 30 could include an alternative twisted fiber, such as an X-STATIC® polyester blended yarn. The sock 10 is knitted with one course 24 of Z-twist core-spun yarn and an adjacent course 24 of S-twist core-spun yarn knitted in a jersey knit pattern, with each yarn serving to cancel the torsional biases of the other yarn. Preferably, the core 28 has about a 40 denier and the sheath 30 has about a 266 denier for each of the compression categories of sock 10. However, it is also within the scope of the present invention where one or more compression categories of sock 10 are made with different deniers of core 28 and/or sheath 30.

TABLE 1

Measured Stretch of Compression Trouser Socks Made with Core-spun and Nylon Yarns.

| | CORE-SPUN | NYLON | CORE-SPUN | NYLON | CORE-SPUN 15-20 mmHg | NYLON | CORE-SPUN | NYLON |
|---|---|---|---|---|---|---|---|---|
| | 15-20 mmHg SMALL | 15-20 mmHg SMALL | 15-20 mmHg MEDIUM | 15-20 mmHg MEDIUM | 15-20 mmHg LARGE | 15-20 mmHg LARGE | 15-20 mmHg X-LARGE | 15-20 mmHg X-LARGE |
| RELAXED ANKLE WIDTH | 2.75" | 3" | 3" | 3" | 3" | 3" | 3.25" | 3" |
| RELAXED CALF WIDTH | 3.75" | 4" | 3.75" | 4.25" | 4" | 4.25" | 4" | 4.50" |
| RELAXED LEG LENGTH | 8" | 12.50" | 8.50" | 13.50" | 9.50" | 14.50" | 10.50" | 15.50" |
| RELAXED FOOT LENGTH | 2.75" | 4.75" | 3" | 5.25" | 3.50" | 6.50" | 3.75" | 6.50" |
| ANKLE RESISTANCE X-STRETCH | 8.25" | 7" | 8.75" | 7.25" | 9.25" | 7.50" | 9.75" | 8" |
| ANKLE MAXIMUM X-STRETCH | 12.75" | 10.75" | 13" | 11.25" | 13.25" | 12" | 13.75" | 12.25" |
| CALF RESISTANCE X-STRETCH | 10.25" | 8.50" | 10.75" | 9" | 11.25" | 9.50" | 11.50" | 9.50" |
| CALF MAXIMUM X-STRETCH | 15.5" | 12.50" | 15.75" | 13.50" | 16" | 14.25" | 17.25" | 14.25" |
| RESISTANCE LEG LENGTH STRETCH | 20" | 18.75" | 21.50" | 21" | 26" | 24" | 28" | 25.50" |
| MAXIMUM LEG LENGTH STRETCH | 22" | 20" | 24.50" | 22" | 28.50" | 25" | 31" | 26.50" |
| RESISTANCE FOOT LENGTH STRETCH | 11.25" | 11.50" | 13" | 12.50" | 14.50" | 17.75" | 15" | 14.25" |
| MAXIMUM FOOT LENGTH STRETCH | 12.25" | 12" | 14" | 13" | 15.50" | 15.25" | 16.50" | 15" |
| | CORE-SPUN | NYLON | CORE-SPUN | NYLON | CORE-SPUN 20-30 mmHg | NYLON | CORE-SPUN | NYLON |
| | 20-30 mmHg SMALL | 20-30 mmHg SMALL | 20-30 mmHg MEDIUM | 20-30 mmHg MEDIUM | 20-30 mmHg LARGE | 20-30 mmHg LARGE | 20-30 mmHg X-LARGE | 20-30 mmHg X-LARGE |
| RELAXED ANKLE WIDTH | 2.75" | 2.75" | 3.25" | 3" | 3.25" | 3.25" | 3.5" | 3.50" |
| RELAXED CALF WIDTH | 4.25" | 4.25" | 4.25" | 4.50" | 4.50" | 4.75" | 4.75" | 5" |
| RELAXED LEG LENGTH | 8.50" | 13.50" | 9.25" | 14" | 10.25" | 14.50" | 10.50" | 15.50" |
| RELAXED FOOT LENGTH | 3.25" | 4.25" | 3.25" | 4.75" | 4.25" | 5" | 4.75" | 5.50" |
| ANKLE RESISTANCE X-STRETCH | 7.25" | 6.75" | 8.75" | 7.25" | 9.25" | 7.50" | 9.50" | 7.50" |
| ANKLE MAXIMUM X-STRETCH | 12.25" | 11.50" | 13.25" | 12.25" | 14.25" | 12.75" | 14.50" | 12.50" |
| CALF RESISTANCE X-STRETCH | 9.50" | 8.75" | 9.75" | 9.25" | 10.25" | 9.25" | 11" | 10" |
| CALF MAXIMUM X-STRETCH | 16" | 14.50" | 16.50" | 14.50" | 17.50" | 14.50" | 17.75" | 15.25" |
| RESISTANCE LEG LENGTH STRETCH | 22.25" | 19.25" | 24" | 22" | 28" | 22" | 30" | 24.75" |
| MAXIMUM LEG LENGTH STRETCH | 24.50" | 20.25" | 26.50" | 23" | 30.50" | 23.50" | 32.50" | 26" |
| RESISTANCE FOOT LENGTH STRETCH | 12" | 11" | 13" | 12.50" | 15.25" | 12.50" | 16.50" | 13" |
| MAXIMUM FOOT LENGTH STRETCH | 13" | 12" | 14" | 12.75" | 16.25" | 13.25" | 17.50" | 14" |
| | CORE-SPUN | NYLON | CORE-SPUN | NYLON | CORE-SPUN 30-40 mmHg | NYLON | CORE-SPUN | NYLON |
| | 30-40 mmHg SMALL | 30-40 mmHg SMALL | 30-40 mmHg MEDIUM | 30-40 mmHg MEDIUM | 30-40 mmHg LARGE | 30-40 mmHg LARGE | 30-40 mmHg X-LARGE | 30-40 mmHg X-LARGE |
| RELAXED ANKLE WIDTH | 2.75" | 2.75" | 3" | 3" | 3.25" | 3.25" | 3.25" | 6.50" |
| RELAXED CALF WIDTH | 4.25" | 4.50" | 4.25" | 4.50" | 4.75" | 4.75" | 5" | 5" |
| RELAXED LEG LENGTH | 10.50" | 12.50" | 11.25" | 13.50" | 13.25" | 14.50" | 13.50" | 15.50" |
| RELAXED FOOT LENGTH | 3.50" | 4" | 3.75" | 4.25" | 4.75" | 5.50" | 5.50" | 6" |
| ANKLE RESISTANCE X-STRETCH | 6.25" | 5.75" | 6.75" | 6" | 7" | 6.75" | 7.25" | 7" |
| ANKLE MAXIMUM X-STRETCH | 11.75" | 11" | 12.50" | 11" | 13" | 12.25" | 13.50" | 12.50" |
| CALF RESISTANCE X-STRETCH | 9.25" | 8.25" | 9.25" | 8.25" | 9.75" | 9.25" | 9.75" | 9.25" |
| CALF MAXIMUM X-STRETCH | 14.75" | 13.75" | 15.25" | 13.50" | 16" | 15.50" | 16" | 15.5" |
| RESISTANCE LEG LENGTH STRETCH | 20.50" | 17" | 21" | 19.50" | 28.25" | 22" | 27.75" | 24" |
| MAXIMUM LEG LENGTH STRETCH | 23.25" | 18" | 24" | 20.50" | 30" | 23" | 31.50" | 25.50" |
| RESISTANCE FOOT LENGTH STRETCH | 13" | 10" | 13" | 11" | 14" | 13" | 15.50" | 14" |
| MAXIMUM FOOT LENGTH STRETCH | 14" | 11" | 14" | 12" | 16" | 14" | 17" | 15" |

The core-spun sock 10 also preferably includes one yarn of laid-in double-covered Lycra® spandex (with a nylon cover) in a 2×2 pattern (i.e., where two needles catch the spandex and two needles stay down) in between adjacent courses 24 of Z-twist and S-twist core-spun yarn. However, the double-covered spandex could include an alternative branded spandex and/or an alternative fiber cover without departing from the scope of the present invention. As shown in Table 2, the preferred denier of the spandex and the preferred denier of the nylon cover around the spandex are determined to provide compression according to the compression category, but it is also within the ambit of the present invention where other deniers of spandex and nylon are used. Additional construction details of the preferred sock 10 are disclosed in Table 2 below. It is also within the scope of the present invention where the sock 10 has an alternative construction, such as an alternate knit pattern (e.g., a 1×1 pattern). Also, an alternative compression sock has been developed with a similar configuration and denier of core-spun yarn and laid-in spandex, but the CoolMax® core-spun yarn is replaced with a polyester X-STATIC® yarn.

The conventional nylon sock used in the stretch comparison presented in Table 1 includes a knitted microfiber yarn.

The 15-20 mmHg compression nylon sock uses a 210 denier nylon, and the 20-30 mmHg and 30-40 mmHg use a 280 denier nylon.

TABLE 2

Construction Example Using Core-spun Yarn

|  | 10-15 mmHg | 15-20 mmHg | 20-30 mmHg | 30-40 mmHg |
|---|---|---|---|---|
| Knit-in core-spun yarn with CoolMax ® polyester sheath and Lycra ® spandex core | core: 40 denier sheath: 266 denier | core: 40 denier sheath: 266 denier | core: 40 denier sheath: 266 denier | core: 40 denier sheath: 266 denier |
| Laid-in spandex covered with nylon | spandex: 120 denier nylon: 40 denier | spandex: 215 denier nylon: 40 denier | spandex: 520 denier nylon: 70 denier | spandex: 720 denier nylon: 70 denier |

From the data in Table 1, it can be determined that the ankle segment of the foot section 18 has a maximum cross-stretch percent elongation that ranges from about 300% to about 360%, and the calf segment of the lower leg section 22 has a maximum cross-stretch percent elongation that ranges from about 220% to about 330%. Additionally, the leg section 22 has a maximum length-stretch percent elongation that ranges from about 120% to about 200%, and the foot section 18 has a maximum length-stretch percent elongation that ranges from about 200% to about 350%. The average increase in stretch of core-spun yarn compared to nylon yarn, as determined from the data in Table 1, is shown in Table 3. Thus, the sock 10 with core-spun yarn surprisingly provides significantly greater stretch elongation compared to the conventional nylon gradient compression sock while maintaining substantially the same compression, and has been found through a wearer survey to be easier to don compared to the nylon sock. Furthermore, it has also been determined that the core-spun yarn unexpectedly provides a fuller and more comfortable knit sock and also conforms better to the leg about areas of movement (e.g., the front of the ankle) when compared to the conventional nylon sock. In particular, it would not be predictable to improve the stretch of the garment by changing the base yarn to a high-elongation yarn (such as core-spun yarn) because the laid-in spandex (or equivalent) yarn is generally understood to be the primary source of compression and resistance to cross-stretch during donning (i.e., that the knitted core-spun yarn would provide a relatively small amount of compression and resistance to cross-stretch). However, we have found that the maximum elongation and elongation under resistance allowed by core-spun yarns, relative to conventional gradient compression hosiery, appears to promote easier donning by a majority of wearers even though the therapeutic compression levels provided by laid-in spandex remain the same.

Furthermore, within the broad art of knitting, hosiery products are typically considered to be fine gauge circular knit products, are generally made of finer denier yarns, and are generally produced on hosiery or fine-gauge sock machines. Conversely, garments made with relatively high denier core-spun yarns are typically made on coarse-gauge equipment (such as flat-bed knitting machines). It would also not be predictable to knit gradient compression hosiery with core-spun-yarns because core-spun yarns generally carry a higher cost point than traditional hosiery yarns, core-spun yarns are not as common as traditional nylons and spandex, and core-spun yarns are available from far fewer yarn manufacturing companies than other yarns. Consequently, there was no perceived advantage to incorporate core-spun yarn into conventional gradient compression hosiery. For the above-noted reasons, it generally would not have been predictable to provide the advantageous and unexpected results explained herein by knitting gradient compression hosiery using core-spun yarns.

Figure 2:
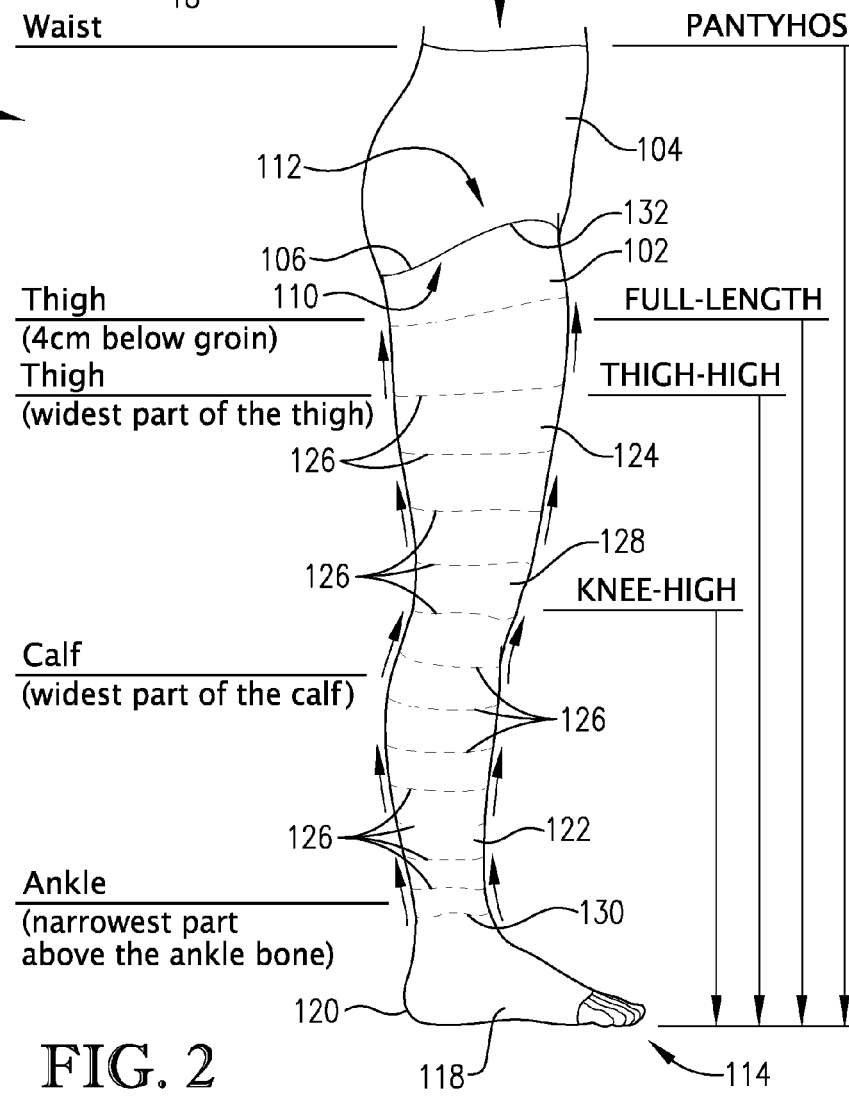
FIG. 2 is a right side view of a knitted gradient compression pantyhose constructed in accordance with a second preferred embodiment of the present invention, showing compression that decreases in the proximal direction from the ankle to the top of the thigh.

Turning to FIG. 2, knitted gradient compression hosiery can be configured in various sizes, such as pantyhose or full-length, thigh-high, or knee-high hosiery (such as trouser socks). The sock 10 and hosiery of other lengths can be sized for a particular patient by measuring the lower limb L at locations along the limb, i.e., at the narrowest part above the ankle, the widest part of the calf, the widest part of the thigh (if necessary), the thigh just below the groin (if necessary), and the waist (if necessary).

TABLE 3

Percent Increase in Stretch of Compression Trouser Socks Made with Core-spun Yarn over Nylon Yarn, Using 5-Pound Resistance

|  | 15-20 mmHg | 20-30 mmHg | 30-40 mmHg |
|---|---|---|---|
| CROSS STRETCH (% greater) [Jones Cross Stretch Machine] |  |  |  |
| Ankle Resistance (5 Lb. Weight) | 21.6% | 19.2% | 6.3% |
| Ankle Maximum | 13.8 | 10.6 | 8.5 |
| Calf Resistance (5 Lb. Weight) | 19.8 | 8.6 | 8.6 |
| Calf Maximum | 18.4 | 15.0 | 6.2 |
| LENGTH STRETCH (% greater) [Length Stretch Machine] |  |  |  |
| Leg Length Resistance | 7.2% | 18.7% | 18.4% |
| Leg Length Maximum | 13.5 | 22.8 | 24.8 |

Turning again to FIG. 2, an alternative knitted gradient compression hosiery 100 is constructed in accordance with a second preferred embodiment of the present invention. For the sake of brevity, the remaining description will focus primarily on the differences of these alternative embodiments from the preferred embodiment described above. The alternative hosiery 100 comprises unitary pantyhose that includes a pair of substantially identical alternative stockings 102 (with only one of the stockings 102 being depicted) arranged side-by-side and a lower torso section 104 attached to both stockings 102 along seams 106 to form the pantyhose. The lower torso section 104 is preferably unitary and presents an upper proximal opening 108 and lower distal openings 110. The stockings 102 present an alternative proximal open end 112 and an alternative distal open toe end 114 that permits the wearer's toes to be exposed, although the toe end 114 could be closed as shown in the first embodiment. The stockings 102 also include an alternative foot section 118, a heel section 120, an alternative lower leg section 122, and an upper leg section 124. The stockings 102 are attached to the lower torso section 104 by positioning the proximal open ends 112 adjacent to corresponding lower distal openings 110 and attaching the stockings 102 and lower torso section 104 along respective seams 106.

Similar to sock 10, the hosiery 100 is weft-knitted with courses 126 of core-spun yarn and also includes integrated elastomeric threads. The hosiery 100 also presents a gradient compression region 128 that extends proximally from a distal location 130 adjacent the heel section 120 (and above the user's ankle A) along the leg sections 122,124 to a proximal location 132 adjacent the proximal open end 112. Again, the gradient compression region 128 provides compression to the limb L that decreases progressively from the distal location 130 to the proximal location 132.

The preferred forms of the invention described above are to be used as illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of the present invention as pertains to any apparatus not materially departing from but outside the literal scope of the invention as set forth in the following claims.

What is claimed is:

1. Gradient compression hosiery operable to be received on the lower limb of a wearer and provide compression to the lower limb that varies along the length of the limb, said gradient compression hosiery comprising:
   a stocking section that extends continuously between a distal end and an open proximal end thereof,
   said stocking section including a tubular foot portion extending from the distal end and a tubular leg portion extending from the open proximal end, with the foot portion dimensioned to receive the foot of the wearer and the leg portion dimensioned to receive at least part of the leg of the wearer when the hosiery is donned,
   said stocking section being knitted at least substantially of a stretch yarn and including elastomeric threads integrated into the stretch yarn knitting, with the foot portion and leg portion being configured to be undersized relative to the foot and leg of the wearer,
   said stocking section presenting a gradient region that extends from a distal location adjacent the distal end to a proximal location adjacent the proximal end, with a property of the hosiery changing progressively along the gradient region to provide compression that decreases progressively from the distal location to the proximal location when the hosiery is donned,
   said stretch yarn comprising a core-spun yarn that includes an a pre-tensioned elastomeric core and a twisted fiber sheath, wherein the core is pre-tensioned when the sheath is twisted around the core.

2. The gradient compression hosiery as claimed in claim 1, said hosiery property comprising a stitch size of the stretch yarn knitting that increases progressively from the distal location to the proximal location.

3. The gradient compression hosiery as claimed in claim 1, said hosiery property being at least partly based upon a percentage draft of the elastomeric core applied while covering the core with the sheath.

4. The gradient compression hosiery as claimed in claim 1, said hosiery property comprising a thread property of the elastomeric threads that changes progressively from the distal location to the proximal location to provide the progressively decreasing compressive pressure.

5. The gradient compression hosiery as claimed in claim 4, said thread property comprising a pre-tension of the elastomeric threads that gradually decreases from the distal location to the proximal location.

6. The gradient compression hosiery as claimed in claim 5, said hosiery including another property comprising a stitch size of the stretch yarn knitting that increases progressively from the distal location to the proximal location.

7. The gradient compression hosiery as claimed in claim 4, said thread property being at least partly based upon a thread denier.

8. The gradient compression hosiery as claimed in claim 1, said hosiery property comprising a measured stocking compression of the stocking section, with the measured stocking compression being determined for a designated circumference of the stocking section.

9. The gradient compression hosiery as claimed in claim 8, said measured stocking compression ranging from about 10 mmHg to about 40 mmHg.

10. The gradient compression hosiery as claimed in claim 1, said gradient region extending above and proximal to the foot portion.

11. The gradient compression hosiery as claimed in claim 10, said leg portion presenting a maximum circumference configured to be located adjacent the widest part of the wearer's thigh, said proximal location of the gradient region extending above and proximal to the maximum circumference.

12. The gradient compression hosiery as claimed in claim 1, said elastomeric core comprising spandex fiber.

13. The gradient compression hosiery as claimed in claim 12, said sheath including non-elastomeric fibers wound about the elastomeric core.

14. The gradient compression hosiery as claimed in claim 13, said non-elastomeric fibers comprising a synthetic polyester yarn.

15. The gradient compression hosiery as claimed in claim 1, said stretch yarn including multiple strands including an equal number of S-twist and Z-twist strands.

16. The gradient compression hosiery as claimed in claim 1, said stocking section including an ankle portion, with the ankle portion having a maximum cross-stretch percent elongation that ranges from about 300% to about 360%.

17. The gradient compression hosiery as claimed in claim 1, said stocking section including a calf segment of the leg portion, with the calf segment having a maximum cross-stretch percent elongation that ranges from about 220% to about 330%.

18. The gradient compression hosiery as claimed in claim 1, said leg portion having a maximum length-stretch percent elongation that ranges from about 120% to about 200%.

19. The gradient compression hosiery as claimed in claim 1, said foot portion having a maximum length-stretch percent elongation that ranges from about 200% to about 350%.

20. The gradient compression hosiery as claimed in claim 1; and
 a lower torso section knitted to the stocking section and another stocking section substantially identical to the first-mentioned stocking section to form pantyhose.

21. The gradient compression hosiery as claimed in claim 1,
 said distal end comprising an open-toe end.

22. The gradient compression hosiery as claimed in claim 1,
 said core-spun yarn including S-twist and Z-twist core-spun yarns,
 said stocking section being knitted with alternating courses of S-twist and Z-twist core-spun yarns.

* * * * *